United States Patent [19]

Ishihara et al.

[11] Patent Number: 4,748,262

[45] Date of Patent: May 31, 1988

[54] (PHENYL DIMETHYL CARBINYL) SILANE COMPOUND AND A METHOD FOR THE PREPARATION THEREOF

[75] Inventors: Toshinobu Ishihara; Minoru Takamizawa; Mikio Endo; Toru Kubota, all of Joetsu, Japan

[73] Assignee: Shin-Etsu Chemical Co., Ltd., Tokyo, Japan

[21] Appl. No.: 91,885

[22] Filed: Sep. 1, 1987

[30] Foreign Application Priority Data

Sep. 4, 1986 [JP] Japan ................................. 61-208337

[51] Int. Cl.$^4$ ............................ C07F 7/08; C07F 7/18
[52] U.S. Cl. .................................... 556/480; 556/482; 556/484; 556/489
[58] Field of Search ................ 556/480, 482, 484, 489

[56] References Cited

U.S. PATENT DOCUMENTS

| 3,334,122 | 8/1964 | Cekada et al. | 556/489 X |
| 3,423,445 | 1/1969 | Holbrook et al. | 556/489 X |
| 4,107,439 | 8/1978 | Walker et al. | 556/482 X |
| 4,116,993 | 9/1978 | Bluestein et al. | 556/480 X |
| 4,135,051 | 1/1979 | Walker | 556/482 X |
| 4,180,515 | 12/1979 | Bargain et al. | 556/480 X |
| 4,242,272 | 12/1980 | Koga et al. | 556/489 X |
| 4,469,881 | 9/1984 | Arkles | 556/484 X |

Primary Examiner—Paul F. Shaver
Attorney, Agent, or Firm—Jules E. Goldberg

[57] ABSTRACT

The invention provides organosilane compounds of a novel class having one or two (phenyl dimethyl carbinyl) groups bonded to the silicon atom as represented by the general formula $(PhMe_2C)_pR_qX_rSi$, in which Ph is a phenyl group, Me is a methyl group, R is a monovalent hydrocarbon group selected from the class consisting of alkyl, alkenyl and aryl groups, X is a halogen atom or an alkoxy group, p is 1 or 2, q is zero, 1 or 2 and r is zero, 1, 2 or 3 with the proviso that $p+q+r=4$. The compound can be prepared by the reaction of a Grignard reagent $PhMe_2C\cdot MgY$, in which Y is a halogen atom, with a silane compound represented by the general formula $R_qSiX_{4-q}$ in an organic solvent.

11 Claims, No Drawings

(PHENYL DIMETHYL CARBINYL) SILANE COMPOUND AND A METHOD FOR THE PREPARATION THEREOF

BACKGROUND OF THE INVENTION

The present invention relates to a novel organosilicon compound and a method for the preparation thereof or, more particularly, to a (phenyl dimethyl carbinyl)silane compound and a method for the preparation thereof.

Among the multitude of known organosilicon compounds, some are distinguished by the substituent group on the silicon atom having great bulkiness with a remarkable effect of steric hindrance. tert-Butyl dimethyl chlorosilane is an example of such organosilicon compounds and is a useful compound as a special selective silylating agent in the synthetic preparation of various sex hormones such as prostaglandins and antibiotics such as chenamycin. This tert-butyl dimethyl chlorosilane can be synthesized by several known methods including a method by utilizing tert-butyl lithium reported in Journal or Organic Chemistry, volume 43, page 3648 (1978) and Journal of the American Chemical Society, volume 76, page 1030 (1954) and a method by utilizing a Grignard reaction. These methods for the preparation of tert-butyl dimethyl chlorosilane are not quite satisfactory as an industrial process because the former method involves a problem of safety due to the dangerous reactants used therein such as metallic lithium and organic lithium compounds while the latter method is performed in a lengthy process as a result of the reaction using a hydrogen silane compound as an intermediate.

Accordingly, it has long been desired to develop a novel organosilicon compound capable of being used as a special silylating agent having one or more of bulky substituent groups with usefulness more than the above mentioned tert-butyl dimethyl chlorosilane and still being prepared without the problems and disadvantages in the synthetic preparation of the tert-butyl dimethyl chlorosilane.

SUMMARY OF THE INVENTION

Therefore, the present invention has an object to provide a novel organosilicon compound to meet the above described requirements as well as a method for the preparation thereof.

The organosilicon compound provided by the present invention is a (phenyl dimethyl carbinyl)silane compound represented by the general formula $$(PhMe_2C)_p R_q X_r Si, \quad (I)$$

in which Ph is a phenyl group, Me is a methyl group, R is a monovalent hydrocarbon group selected from the class consisting of alkyl groups, alkenyl groups and aryl groups, X is a halogen atom or an alkoxy group, p is 1 or 2, q is zero, 1 or 2 and r is zero, 1, 2 or 3 with the proviso that $p+q+r=4$.

The above defined (phenyl dimethyl carbinyl)silane compound represented by the general formula (I) can be prepared by the reaction of a Grignard reagent phenyl dimethyl carbinyl magnesium halide represented by the general formula $$PhMe_2C.MgY, \quad (II)$$

in which Ph and Me each have the same meaning as defined above and Y is a halogen atom, with a silane compound represented by the general formula $$R_q SiX_{4-q}, \quad (III)$$

in which each symbol has the same meaning as defined above.

DETAILED DESCRIPTION OF THE PREFERRED EMBODIMENTS

As is defined in the above given summary of the invention, the (phenyl dimethyl carbinyl)silane compound of the invention characteristically has one or two or, preferably, one phenyl dimethyl carbinyl group bonded to the silicon atom in a molecule, the other three or two substituent groups on the silicon atom being selected from the class consisting of alkyl groups, alkenyl groups, aryl groups, alkoxy groups and halogen atoms. The group denoted by R is an alkyl group such as methyl and ethyl groups, alkenyl group such as vinyl and allyl groups or aryl group such as phenyl and tolyl groups. These monovalent hydrocarbon groups as R may be substituted with halogen atoms or other substituent groups for a part or all of the hydrogen atoms therein. When a molecule of the (phenyl dimethyl carbinyl)silane compound has two R groups, they can be of the same kind or can be of different kinds each from the other. The symbol X in the general formula (I) denotes an atom of halogen such as chlorine, bromine and iodine with preference of chlorine or an alkoxy group such as methoxy and ethoxy groups. When a single molecule of the (phenyl dimethyl carbinyl)silane compound has two or three groups denoted by X, they can be of the same kind or can be of different kinds each from the others.

Particular examples of the inventive (phenyl dimethyl carbinyl)silane compound defined above include, for example, dimethyl(phenyl dimethyl carbinyl)chlorosilane, methyl phenyl(phenyl dimethyl carbinyl)chlorosilane, dimethyl di(phenyl dimethyl carbinyl)silane, methyl(phenyl dimethyl carbonyl)dichlorosilane, methyl di(phenyl dimethyl carbinyl)chlorosilane, vinyl methyl(phenyl dimethyl carbinyl)chlorosilane, vinyl methyl di(phenyl dimethyl carbinyl)silane, phenyl(phenyl dimethyl carbinyl)dichlorosilane, phenyl di(phenyl dimethyl carbinyl)chlorosilane, diphenyl(phenyl dimethyl carbinyl)chlorosilane, diphenyl di(phenyl dimethyl carbinyl)silane, chloromethyl methyl(phenyl dimethyl carbinyl)chlorosilane, chloromethyl methyl di(phenyl dimethyl carbinyl)silane, methyl(phenyl dimethyl carbinyl)methoxy chlorosilane, methyl di(phenyl dimethyl carbinyl)methoxy silane, methyl(phenyl dimethyl carbinyl)dimethoxy silane, phenyl(phenyl dimethyl carbinyl)diethoxy silane, phenyl di(phenyl dimethyl carbinyl)ethoxy silane, and the like.

One of the starting reactants in the synthetic preparation of the above described (phenyl dimethyl carbinyl)silane compound is the Grignard reagent phenyl dimethyl carbinyl magnesium halide represented by the general formula (II). This Grignard reagent can be readily prepared by the reaction of metallic magnesium in an inert organic solvent with a phenyl dimethyl carbinyl halide of the formula PhMe₂CY, in which each symbol has the same meaning as defined above. This compound is a reaction product obtained by heating a mixture of α-methyl styrene and an aqueous solution of hydrogen halide. It should be noted that the phenyl dimethyl carbinyl halide prepared in this manner is thermally unstable and readily dehalogenated to return to the methyl styrene during distillation so that it is essential that the phenyl dimethyl carbinyl halide as prepared should be immediately separated from the aqueous reaction medium.

Further, the phenyl dimethyl carbinyl magnesium halide of the general formula (II) may react in the organic solvent with the starting phenyl dimethyl carbinyl halide according to the following reaction equation

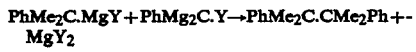

to increase the concentration of impurities in the solvent so that it is essential that the Grignard reagent should be brought into reaction with the organosilane compound of the general formula (III) as quickly as possible by preventing the above mentioned side reaction.

The thus obtained Grignard reagent of the general formula (II) is reacted with the organosilane compound of the general formula (III) according to the following reaction equation:

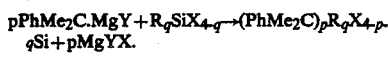

The organosilane compound of the general formula (II) is exemplified by dimethyl dichlorosilane, methyl trichlorosilane, vinyl methyl dichlorosilane, phenyl trichlorosilane, diphenyl dichlorosilane, methyl trimethoxy silane, phenyl ethoxy silane, chloromethyl methyl dichlorosilane and the like.

It should be noted in carrying out the above described reaction that the formation of the Grignard reagent and the reaction of the same with the organosilane compound should proceed concurrently so that the phenyl dimethyl carbinyl halide and the organosilane compound should be introduced simultaneously into the mixture of metallic magnesium and an inert organic solvent. When this procedure is not followed, no industrially feasible yield of the desired compound could be obtained.

It is generally accepted that introduction of a tertiary hydrocarbon group into a silicon atom proceeds only by use of an alkyl lithium reagent and not with a Grignard reagent. On the other hand, it is also understood that a Grignard reagent can react with a silicon compound only when the silicon compound has a hydrogen atom directly bonded to the silicon atom. In contrast to the above mentioned general knowledge in the chemistry of organosilicon compounds, it is a quite unexpected discovery that the above described reaction with the Grignard reagent can proceed readily to introduce the phenyl dimethyl carbinyl group, a tertiary hydrocarbon group, into the silicon atom of the organosilane compound even when the organosilane compound has no silicon-bonded hydrogen atom.

The above described reactions for the preparation of the inventive novel silane compound, i.e. the reaction for the formation of the Grignard reagent of the general formula (II) and the reaction of the same with the organosilane compound of the general formula (III), should be performed in an inert organic solvent which is exemplified by ether solvents such as diethyl ether, tetrahydrofuran and the like and hydrocarbon solvents such as benzene, toluene and the like. If desired, these organic solvents can be used as a mixture of two kinds or more. The reaction is performed at a temperature in the range from 10° to 150° C. or, preferably, from 30° to 100° C. The reaction should be performed under an atmosphere of an inert gas such as nitrogen, argon and the like. In particular, ocxgen should be excluded from the atmosphere since oxygen may react with the Grignard reagent in the course of the reaction to cause remarkable decrease in the yield of the desired novel organosilicon compound.

The novel (phenyl dimethyl carbinyl)silane compound provided by the invention has a highly bulky substituent group in the molecule so that it is useful as a special silylating agent in the synthetic preparation of some pharmaceutical compounds such as steroids, prostaglandins and the like by utilizing the feature that the silyl ether linkages obtained by the reaction with an alcohol are chemically stable. The compound provided by the invention is also useful as a catalyst or additive for the polymerization of an olefin into a stereospecific polymer.

In the following, detailed description is given by way of examples on the synthetic preparation and characterization of the novel (phenyl dimethyl carbinyl)silane compounds of the invention.

EXAMPLE 1

Into 12 g (0.5 mole) of metallic magnesium in 600 ml of tetrahydrofuran kept at a temperature of 40° to 50° C. under agitation were added dropwise a mixture of 64.5 g (0.5 mole) of dimethyl dichlorosilane and 77.3 g (0.5 mole) of phenyl dimethyl carbinyl chloride under a stream of nitrogen gas. After completion of the dropwise addition of the reactant mixture, the temperature of the reaction mixture in the reaction vessel was maintained at 50° C. and agitation was continued for additional 1 hour. The reaction mixture was then filtered and the filtrate was concentrated by evaporation of the solvent and distilled under reduced pressure to give 90.3 g of an oily material as a fraction boiling at 74° C. under a pressure of 2 mmHg. Gas chromatographic analysis of this material using a 15%-coated 2-meters long packed column of SE-30 indicated that this material was composed of a single compound. The results of the mass spectrometric analysis, NMR spectrometric analysis and infrared absorption spectrophotometric analysis shown below supported that this product was (phenyl dimethyl carbinyl)dimethyl chlorosilane of the structural formula (PhMe$_2$C)Me$_2$SiCl.

Mass spectrometric data: m/e (relative intensity) 212(16)*; 197(3)*; 177(3); 135(3); 119(100); 118(56); 93(34)*; 91(43); 79(8); 78(8); 77(11); 65(8); 41(18); 39(8). Note: the peak with an asterisk corresponds to $^{35}$Cl and is accompanied by a peak corresponding to $^{37}$Cl.

NMR spectrometric data: δ (ppm)

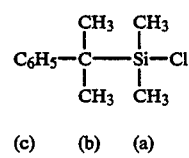

(a): 0.22(s); (b): 1.40(s); (c): 6.80–7.20(m).

Infrared absorption spectrophotometric data: wave number (cm$^{-1}$) 3050; 2970; 2875; 1600; 1500; 1475; 1370; 1260; 1040; 920; 840; 810; 790; 700.

EXAMPLE 2

Into a mixture of 10 g (0.1 mole) of cyclohexanol, 100 ml of N,N-dimethyl formamide and 10.1 g of triethyl amine at room temperature were added dropwise 21.25 g (0.1 mole) of (phenyl dimethyl carbinyl)dimethyl chlorosilane to effect the reaction and the reaction mixture was filtered, concentrated by evaporation of the solvent and distilled under reduced pressure to give a silyl ether compound (phenyl dimethyl carbinyl)-dimethyl cyclohexyloxy silane, which is referred to as the silyl ether A hereinbelow.

Similarly, cyclohexanol was silylated with tert-butyl dimethyl chlorosilane to give another silyl ether compound tert-butyl dimethyl cyclohexyloxy silane, which is referred to as the silyl ether B hereinbelow.

Each of the silyl ethers A and B was added to ethyl alcohol containing 1% by weight of concentrated hydrochloric acid in such an amount as to make a concentration of 10% by weight in the resulting solution which was kept standing at room temperature for 10 minutes. Thereafter, the solution was analyzed by the gas chromatography to determine the decrease in the concentration of the respective silyl ether compound. The results were that the decrease in the concentration of the silyl ether A was 52% after 10 minutes while the silyl ether B had almost completely disappeared.

EXAMPLE 3

The same experimental procedure as in Example 1 was repeated excepting replacement of 64,5 g of the dimethyl dichlorosilane with 74.8 g (0.5 mole) of methyl trichlorosilane to give 86 g of an oily product boiling at 78° C. under a pressure of 2 mmHg. The gas chromatographic analysis indicated that this product was composed of a single compound. The results of the mass spectrometric analysis, NMR spectrometric analysis and infrared absorption spectrophotometric analysis shown below supported that this product was (phenyl dimethyl carbinyl)methyl dichlorosilane of the structural formula $(PhMe_2C)MeSiCl_2$.

Mass spectrometric data: m/e (relative intensity) 232(9)*; 217(0.5)*; 197(1)*; 119(100); 103(8); 91(41); 79(8); 78(8); 77(9); 65(4); 63(5)*; 51(5); 41(8). Note: the peak with an asterisk corresponds to $^{35}Cl$ and is accompanied by a peak corresponding to $^{37}Cl$.

NMR spectrometric data: δ (ppm)

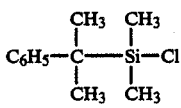

(a): 0.54(s); (b): 1.5(s); (c): 6.90–7.20(m).

Infrared absorption spectrophotometric data: wave number (cm$^{-1}$) 3050; 2960; 2870, 1600; 1500; 1470; 1450; 1370; 1260; 1135; 1040; 920; 900; 700.

EXAMPLE 4

The same experimental procedure as in Example 1 was repeated excepting replacement of 64.5 g of the dimethyl dichlorosilane with 95.5 g (0.5 mole) of phenyl methyl dichlorosilane and replacement of 600 ml of tetrahydrofuran with a mixture of 300 ml of tetrahydrofuran and 300 ml of toluene to give 96 g of an oily product boiling at 130° C. under a pressure of 2 mmHg. The gas chromatographic analysis indicated that this product was composed of a single compound. The results of the mass spectrometric anal-sis, NMR spectrometric analysis and infrared absorption spectrophotometric analysis shown below supported that this product was (phenyl dimethyl carbinyl)methyl phenyl chlorosilane of the structural formula $(PhMe_2C)MePhSiCl$.

Mass spectrometric data: m/e (relative intensity) 274(18)*; 155(100)*; 119(36); 118(51); 103(6); 91(29); 79(5); 78(5); 77(6); 65(4); 63(10)*; 51(4); 41(9). Note: the peak with an asterisk corresponds to $^{35}Cl$ and is accompanied by a peak corresponding to $^{37}Cl$.

NMR spectrometric data: δ (ppm)

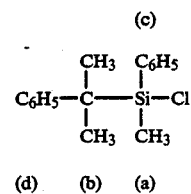

(a): 0.5(s); (b): 1.4(w); (c): 6.80–7.05(m); (d) 7.04–7.30(m) J=6 cps.

Infrared absorption spectrophotometric data: wave number (cm$^{-1}$) 3050; 2960; 2870; 1600; 1500; 1440; 1370; 1260; 1120; 1040; 920; 700.

EXAMPLE 5

(Phenyl dimethyl carbinyl)methyl dimethoxy silane of the formula $(PhMe_2C)MeSi(OMe)_2$ was synthesized in about the same manner as in Example 1 from methyl trimethoxy silane and the Grignard reagent. The mass spectrometric data of the compound were as follows.

Mass spectrometric data: m/e (relative intensity) 224(9); 203(0.5); 119(2); 118(4); 117(3); 107(5); 106(9); 105(100); 91(5); 75(25); 59(5).

EXAMPLE 6

(Phenyl dimethyl carbinyl)phenyl dichlorosilane of the structural formula $(PhMe_2C)PhSiCl_2$ was synthesized in about the same manner as in Example 1 from phenyl trichlorosilane and the Grignard reagent. The mass spectrometric data of the compound were as follows.

Mass spectrometric data: m/e (relative intensity) 234(7)*; 175(6)*; 120(10); 119(100); 118(22); 103(7); 91(30); 79(6); 78(6); 77(15); 65(3); 63(4)*; 51(6); 41(10). Note: the peak with an asterisk corresponds to $^{35}Cl$ and is accompanied by a peak corresponding to $^{37}Cl$.

EXAMPLE 7

(Phenyl dimethyl carbinyl)methyl vinyl dichlorosilane of the structural formula $(PhMe_2C)(CH_2=CH-)MeSiCl$ was synthesized in about the same manner as in Example 1 from methyl vinyl dichlorosilane and the Grignard reagent. The mass spectrometric data of the compound were as follows.

Mass spectrometric data: m/e (relative intensity) 224(20)*; 155(7)*; 120(10); 119(100); 118(53); 107(10); 105(27); 91(37); 79(17); 65(5); 63(3)*; 51(3); 41(1). Note: the peak with an asterisk corresponds to $^{35}Cl$ and is accompanied by a peak corresponding to $^{37}Cl$.

EXAMPLE 8

(Phenyl dimethyl carbinyl)diphenyl chlorosilane of the structural formula $(PhMe_2C)Ph_2SiCl$ was synthesized in about the same manner as in Example 1 from diphenyl dichlorosilane and the Grignard reagent. The mass spectrometric and NMR spectrometric data of the compound were as follows.

Mass spectrometric data: m/e (relative intensity) 336(8)*; 217(100)*; 181(3); 119(7); 118(12); 91(10); 78(3); 77(6); 65(4); 63(10)*. Note: the peak with an asterisk corresponds to $^{35}$Cl and is accompanied by a peak corresponding to $^{37}$Cl.

NMR spectrometric data: δ (ppm)

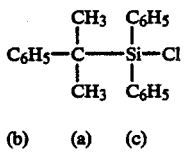

(a) 1.50(s); (b): 6.95–6,75(m); (c): 7.35–7.05(m).

What is claimed is:

1. A (phenyl dimethyl carbinyl)silane compound represented by the general formula $$(PhMe_2C)_p R_q X_r Si,$$

in which Ph is a phenyl group, Me is a methyl group, R is a monovalent hydrocarbon group selected from the class consisting of alkyl groups, alkenyl groups and aryl groups, X is a halogen atom or an alkoxy group, p is 1 or 2, q is zero, 1 or 2 and r is zero, 1, 2 or 3 with the proviso that $p+q+r=4$.

2. The (phenyl dimethyl carbinyl)silane compound as claimed in claim 1 wherein p is 1.

3. The (phenyl dimethyl carbinyl)silane compound as claimed in claim 1 wherein R is selected from the class consisting of methyl, ethyl, vinyl, allyl, phenyl and tolyl groups.

4. (Phenyl dimethyl carbinyl)dimethyl chlorosilane expres-sed by the structural formula (PhMe$_2$C)Me$_2$SiCl, in which Ph is a phenyl group and Me is a methyl group.

5. (Phenyl dimethyl carbinyl)methyl dichlorosilane expres-sed by the structural formula (PhMe$_2$C)MeSiCl$_2$, in which Ph is a phenyl group and Me is a methyl group.

6. (Phenyl dimethyl carbinyl)methyl phenyl chlorosilane expressed by the structural formula (PhMe$_2$C)MePhSiCl, in which Ph is a phenyl group and Me is a methyl group.

7. (Phenyl dimethyl carbinyl)methyl dimethoxy silane expressed by the structural formula (PhMe$_2$C)MeSi(OMe)$_2$, in which Ph is a phenyl group and Me is a methyl group.

8. (Phenyl dimethyl carbinyl)phenyl dichlorosilane expres-sed by the structural formula (PhMe$_2$C)PhSiCl$_2$, in which Ph is a phenyl group and Me is a methyl group.

9. (Phenyl dimethyl carbinyl)methyl vinyl chlorosilane expressed by the structural formula (PhMe$_2$C)(CH$_2$=CH)MeSiCl, in which Ph is a phenyl group and Me is a methyl group.

10. (Phenyl dimethyl carbinyl)diphenyl chlorosilane expres-sed by the structural formula (PhMe$_2$C)Ph$_2$SiCl, in which Ph is a phenyl group and Me is a methyl group.

11. A method for the preparation of a (phenyl dimethyl carbinyl)silane compound represented by the general formula $$(PhMe_2C)_p R_q X_r Si,$$

in which Ph is a phenyl group, Me is a methyl group, R is a monovalent hydrocarbon group selected from the class consisting of alkyl groups, alkenyl groups and aryl groups, X is a halogen atom or an alkoxy group, p is 1 or 2, q is zero, 1 or 2 and r is zero, 1, 2 or 3 with the proviso that $p+q+r=4$, which comprises reacting a Grignard reagent of phenyl dimethyl carbinyl magnesium halide represented by the general formula $$PhMe_2C.MgY,$$

in which Ph and Me each have the same meaning as defined above and Y is a halogen atom, with a silane compound represented by the general formula $$R_q SiX_{4-q},$$

in which each symbol has the same meaning as defined above, in an organic solvent.

* * * * *